US010138458B2

(12) United States Patent
Belgrader et al.

(10) Patent No.: US 10,138,458 B2
(45) Date of Patent: Nov. 27, 2018

(54) MAGNETIC LYSIS METHOD AND DEVICE (71) Applicant: AKONNI BIOSYSTEMS, INC., Frederick, MD (US)

(72) Inventors: Phillip Belgrader, Livermore, CA (US); Benjamin Hindson, Livermore, CA (US)

(73) Assignee: Akonni Biosystems, Inc., Frederick, MD (US)

( * ) Notice: Subject to any disclaimer, the term of this patent is extended or adjusted under 35 U.S.C. 154(b) by 0 days.

(21) Appl. No.: 14/978,562

(22) Filed: Dec. 22, 2015

(65) Prior Publication Data

US 2016/0215255 A1 Jul. 28, 2016

Related U.S. Application Data (60) Continuation of application No. 14/952,391, filed on Nov. 25, 2015, now abandoned, which is a division of application No. 13/765,399, filed on Feb. 12, 2013, now Pat. No. 9,217,174, which is a continuation of application No. 12/886,144, filed on Sep. 20, 2010, now Pat. No. 8,399,190.

(60) Provisional application No. 61/272,396, filed on Sep. 21, 2009.

(51) Int. Cl.
C12M 1/00 (2006.01)
C12N 1/06 (2006.01)
C12N 13/00 (2006.01)
C12Q 1/6806 (2018.01)
C12N 1/20 (2006.01)

(52) U.S. Cl.
CPC .............. *C12N 1/066* (2013.01); *C12N 1/20* (2013.01); *C12N 13/00* (2013.01); *C12Q 1/6806* (2013.01)

(58) Field of Classification Search
USPC ................. 435/6.1, 6.11, 91.1, 287.1, 287.2; 422/50, 68.1
See application file for complete search history.

(56) References Cited

U.S. PATENT DOCUMENTS

| 4,227,815 | A  | 10/1980 | Hoffa            |
| 5,536,475 | A  | 7/1996  | Moubayed et al.  |
| 6,176,609 | B1 | 1/2001  | Cleveland et al. |
| 6,632,662 | B1 | 10/2003 | Broyer et al.    |
| 8,399,190 | B2 | 3/2013  | Belgrader et al. |

(Continued)

FOREIGN PATENT DOCUMENTS

| EP | 1234832 A2   | 8/2002 |
| EP | 1 650 297 A2 | 4/2006 |

(Continued)

OTHER PUBLICATIONS

European Search Report of Application No. 16166269.7, dated Aug. 18, 2016.

(Continued)

*Primary Examiner* — Frank W Lu
(74) *Attorney, Agent, or Firm* — Michael Ya; Morris, Manning & Martin, LLP (57) ABSTRACT A method for lysing cells is disclosed. The method includes stirring cells with a magnetic stir element in the presence of a plurality of cell lysis beads at a speed sufficient to lyse the cells. Also disclosed is a device for lysing cells. The device includes a container having a magnetic stir element and a plurality of cell lysis beads disposed therein. The container is dimensioned to allow rotation of the magnetic stir element inside the container.

8 Claims, 10 Drawing Sheets (56) References Cited

U.S. PATENT DOCUMENTS

| | | | |
|---|---|---|---|
| 2003/0203491 A1 | 10/2003 | Andrevski et al. |
| 2004/0082779 A1 | 4/2004 | Vos et al. |
| 2007/0247968 A1 | 10/2007 | Cleveland |
| 2008/0063628 A1 | 3/2008 | Davis et al. |
| 2008/0102479 A1 | 5/2008 | Merza |

FOREIGN PATENT DOCUMENTS

| | | |
|---|---|---|
| EP | 2083069 | 7/2009 |
| JP | 2001-054727 A | 2/2001 |
| JP | 2002-521023 A | 7/2002 |
| WO | 2009/092662 A1 | 7/2009 |

OTHER PUBLICATIONS

Extended European Search Report, European Patent Application No. 10 817 590.2, dated Nov. 4, 2014.
File history of U.S. Appl. No. 12/886,144, filed Sep. 20, 2010.
"Stir bar" and "Magnetic stirrer" from Wikipedia, the free encyclopedia, printed on Sep. 26, 2012.
Honaker, et al., "Unique Roles of DosT and DosS in DosR Regulon Induction and *Mycobacterium tuberculosis* Dormancy," Infection and Immunity, Aug. 2009, vol. 77, pp. 3258-3263.
International Search Report, International Patent Application No. PCT/US2010/002569, dated Jun. 10, 2011.
International Search Report, Written Opinion, International Patent Application No. PCT/US2010/002569, dated Jun. 10, 2011.
Lui, et al., "Nucleic Acid-Based Detection of Bacterial Pathogens Using Integrated Microfluidic Platform Systems," Sensors, 2009, vol. 9, pp. 3713-3744.
Smolen, et al., "L-Selection Signaling of Neutophil Adhesion and Degranulation Involves p38 Mitogen-Activated Protein Kinase," The Journal of Biological Chemistry, May 2000, vol. 275, No. 21, pp. 15876-15884.
Trotman, et al., "Calcium Alginate Bead Immobilization of Cells Containing Tyrosine Ammonia Lyase Activitry for Use in the Production of p-Hydroxycinnamic Acid," Biotechnology Progress, 2007, vol. 23, pp. 638-644.
Dittrich, et al., "Micro Total Analysis Systems. Latest Advancements and Trends," Anal. Chemistry, 2006, vol. 78. pp. 3887-3908.
Extended European Search Report issued in European Patent Application No. 10 81 7590, dated Sep. 2, 2013.
U.S. Appl. No. 14/952,391, filed Nov. 25, 2015, Abandoned.
U.S. Appl. No. 13/765,399, filed Feb. 12, 2014, Patented.
U.S. Appl. No. 12/886,144, filed Sep. 20, 2010, Patented.

MAGNETIC LYSIS METHOD AND DEVICE

This application is a continuation application of U.S. patent application Ser. No. 14/952,391, filed on Nov. 25, 2015, now abandoned, which is a divisional application of U.S. patent application Ser. No. 13/765,399, filed on Feb. 12, 2013, now U.S. Pat. No. 9,217,174, which is a continuation application of U.S. patent application Ser. No. 12/886,144, filed on Sep. 20, 2010, now U.S. Pat. No. 8,399,190, which claims the priority of U.S. Provisional Application No. 61/272,396, filed on Sep. 21, 2009. The entirety of all of the aforementioned applications is incorporated herein by reference.

FIELD

The technical field is biotechnology and, more specifically, methods and apparatus for lysing cells.

BACKGROUND

Cell lysis is the destruction, or disruption, of a cell's membrane or wall, which breaks open the cell and exposes its contents. Many techniques are available for the disruption of cells, including physical, chemical (e.g., detergent-based methods, chaotropic salts) and biochemical (e.g., enzymes such as lysozyme). Mechanical lysis, such as vortexing and bead-beating, is one form of physical lysis. Sonication is another form of physical lysis, which uses pulsed, high frequency sound waves to agitate and lyse cells, bacteria, spores, and finely diced tissue. These approaches, however, are not readily compatible with an integrated low-cost cell lysis/nucleic acid analysis system. Detergent-based methods are often easier to use with more efficient protocols than physical methods. Nonetheless, the presence of detergent may interfere with downstream reactions in an integrated system and can give variable lysis efficiencies for hardier bacteria and spores and require long incubation steps and or heat treatment. Therefore, there still exists a need for cell lysis methods that are cost-effective, efficient and compatible with an integrated cell lysis/analysis system.

SUMMARY

A method for lysing cells, virus particles and spores is disclosed. The method comprises stirring cells with a magnetic stir element in a container in the presence of a plurality of cell lysis beads, wherein the stir element rotates at a speed sufficient and duration to lyse the cells. In some embodiments, the cell lysis beads are selected from the group consisting of polymer beads, glass beads, ceramic beads and metal beads. In some embodiments, the cell lysis beads have diameters within the range of 10-1000 µm. In some embodiments, 1 mg-10 g of cell lysis beads are added to the lysis chamber. In some embodiments, 1 ul-10 ml of an aqueous liquid is added to the lysis chamber. In some embodiments, a sample or specimen is added directly to the lysis chamber alone. In some embodiments, a sample is added directly to the lysis chamber together with an aqueous liquid (e.g. a solid specimen that is homogenized and lysed to yield an aqueous form). In some embodiments, the magnetic stir element has a rectangular shape, a trapezoidal shape, a two-pronged tuning fork shape, a rod shape, and a bar shape. In some embodiments, the cells are eukaryotic cells, prokaryotic cells, endo-spores, or a combination thereof, and are suspended in a liquid medium at a concentration ranging from 1 to $1\times10^{10}$ cells/ml. In some embodiments, the cells are virus particles and are suspended in a liquid medium at a concentration ranging from 1 to $1\times10^{13}$ particles/ml.

Also disclosed is a method for lysing cells and virus particles. The method comprises suspending cells or virus particles in a liquid medium to form a suspension, and stirring the suspension with a magnetic stir element at high speed, between 1000-5000 rpm, preferably closer to 5000 rpm, in the presence of a plurality of cell lysis beads for a time period between 1-600 seconds, preferably about 90-120 seconds.

Also disclosed is a device for lysing cells and virus particles. The device includes a chamber having one or more magnetic stir elements and a plurality of cell lysis beads disposed therein. The chamber is dimensioned to allow rotation of the one or more magnetic stir elements inside the chamber. In some embodiments, the device further includes a magnetic stirrer that produces a rotating magnetic field, wherein the one or more magnetic stir elements rotate inside the chamber when placed within the operational range of the rotating magnetic field. In some embodiments, the device further includes a chamber holder configured to hold the chamber within the rotating magnetic field produced by the magnetic stirrer.

Also disclosed is a method for purifying nuclei acid from a cell. The method comprises applying a magnetic field to a vessel containing a cell, a stir element, and a plurality of beads, wherein the magnetic field causes the stir element to collide with the plurality of beads and produce a cell lysate; and isolating nuclei acid from the cell lysate.

Also disclosed is a method for amplifying a polynucleotide from a cell. The method comprises applying a magnetic field to a vessel containing a cell, a stir element, and a plurality of beads, wherein the magnetic field causes the stir element to collide with the plurality of beads and produce a cell lysate, and amplifying a polynucleotide from the cell lysate.

Also disclosed is a method for detecting a polynucleotide from a cell. The method comprises applying a magnetic field to a vessel containing a cell, a stir element, and a plurality of beads, wherein the magnetic field causes the stir element to collide with the plurality of beads and produce a cell lysate, and detecting a polynucleotide from the cell lysate. In certain embodiments, the detecting step comprises isolating nuclei acids from the cell lysate, amplifying the polynucleotide from isolated nuclei acids, and detecting the amplified polynucleotide.

BRIEF DESCRIPTION OF DRAWINGS

The detailed description will refer to the following drawings in which:

FIG. 7 is a graph showing real-time PCR amplification of a specific genomic region from unlysed * the cell lysis beads are irregularly shaped particles. In some embodiments, the cell lysis beads are particles with protrusions. In certain embodiments, the amount of beads added to each lysis container is in the range of 1-10,000 mg, 1-1000 mg, 1-100 mg, 1-10 mg, among others.

In certain embodiments, the cell lysis beads have diameters in the range of 10-1,000 μm, 20-400 μm, or 50-200 μm, among others.

The magnetic stir element can be of any shape and should be small enough to be placed into the container and to move or spin or stir within the container. The magnetic stir element can be a bar-shaped, cylinder-shaped, cross-shaped, V-shaped, triangular, rectangular, rod or disc-shaped stir element, among others. In some embodiments, the magnetic stirring element has a rectangular shape. In some embodiments, the magnetic stirrer has a two-pronged tuning fork shape. In some embodiments, the magnetic stirrer has a V-like shape. In some embodiments, the magnetic stirrer has a trapezoidal shape. In certain embodiments, the longest dimension of the stir element is slightly smaller than the diameter of the container (e.g. about 75-95% of the diameter of the container). In certain embodiments, the magnetic stir element is coated with a chemically inert material, such as polymer, glass, or ceramic (e.g., porcelain). In certain embodiments, the polymer is a biocompatible polymer such as PTFE and paralyne.

The cell suspension, cell lysis beads and the magnetic stir element may be placed into the chamber in any order. In some embodiments, the cell suspension is added to the chamber before the cell lysis beads and the magnetic stirring element. In other embodiments, the cell lysis beads and/or the magnetic stirring element are placed into the chamber before the cells (e.g., before a cell suspension).

The chamber, and particularly the cells, beads, and magnetic stir element, are located within an operational range of a varying magnetic field. For example, the chamber may be located with an operational range of a rotating magnetic field (e.g., by placing the container on or adjacent to a magnetic stirrer). The varying magnetic field drives motion of the stir element, such as rotational motion, reciprocation, or a combination thereof, among others, which in turn drives motion of the beads, the cells, and the liquid medium. In some embodiments, the cell suspension is stirred with the magnetic stirring element at a rotation speed and for durations sufficient to lyse the cells inside the container. The appropriate rotation speed and duration are application dependent and can be empirically determined by a person of ordinary skill in the art. Generally speaking, the rotation speed sufficient to lyse the cells is determined by factors such as the type of cells, the concentration of cell suspension, the volume of the cell suspension, the size and shape of the magnetic stirring element, the amount/number, size, shape and hardness of the cell lysis beads, and the size and shape of the chamber.

In certain embodiments, the magnetic stirring element is rotating at a speed between 1000-6000 rpm, preferably about 5000 rpm, for a time period between 1-600 seconds, preferably about 90-120 seconds. In certain embodiments, a chamber (e.g., in the shape of a test tube or micro centrifuge tube) is placed in a rack on a magnetic stirrer (e.g., VP 710C1 Rotary Magnetic Tumble Stirrer, 5000 RPM, 14cm Long Usable Stirring Deck, With Motor Housing And Plate Holder, Stirs 2 Deep Well Microplates Or 6 Standard Microplates—115 Volts AC—60 Hz, V&P Scientific) and is stirred at the highest speed setting (>1000 rpm). In other embodiments, the chamber is a well in a microplate, such as an ELISA plate. In other embodiments, the chamber is a cylinder shaped chamber with a cell inlet and a cell outlet.

In certain embodiments, the varying magnetic field is generated by rotating a magnet, preferably a permanent magnet, in the proximity of magnetic stir element. The magnet may be rotated above, below or by the side of the lysis chamber about an axis that passes through the center of the magnet. In certain embodiments, the chamber or chambers are placed at a position that is vertical to the surface the chamber or the chambers reside on and the magnet is rotated about an axis that is also vertical to the surface the chamber or the chambers reside on. In other embodiments, the chamber or chambers are placed at a position that is vertical to a the surface the chamber or the chambers reside on and the magnet is rotated about an axis that is parallel to the surface the chamber or the chambers reside on. In yet other embodiments, the chamber or chambers are placed at a position that is vertical to a the surface the chamber or the chambers reside on and the magnet is rotated about an axis that forms an angle with the surface the chamber or the chambers reside on. The angle is greater than 0 degree but smaller than 180 degrees. In other embodiments, the magnet also has an elongated shape and rotates about an axis that extends along the longest dimension of the magnet.

Figure 1:
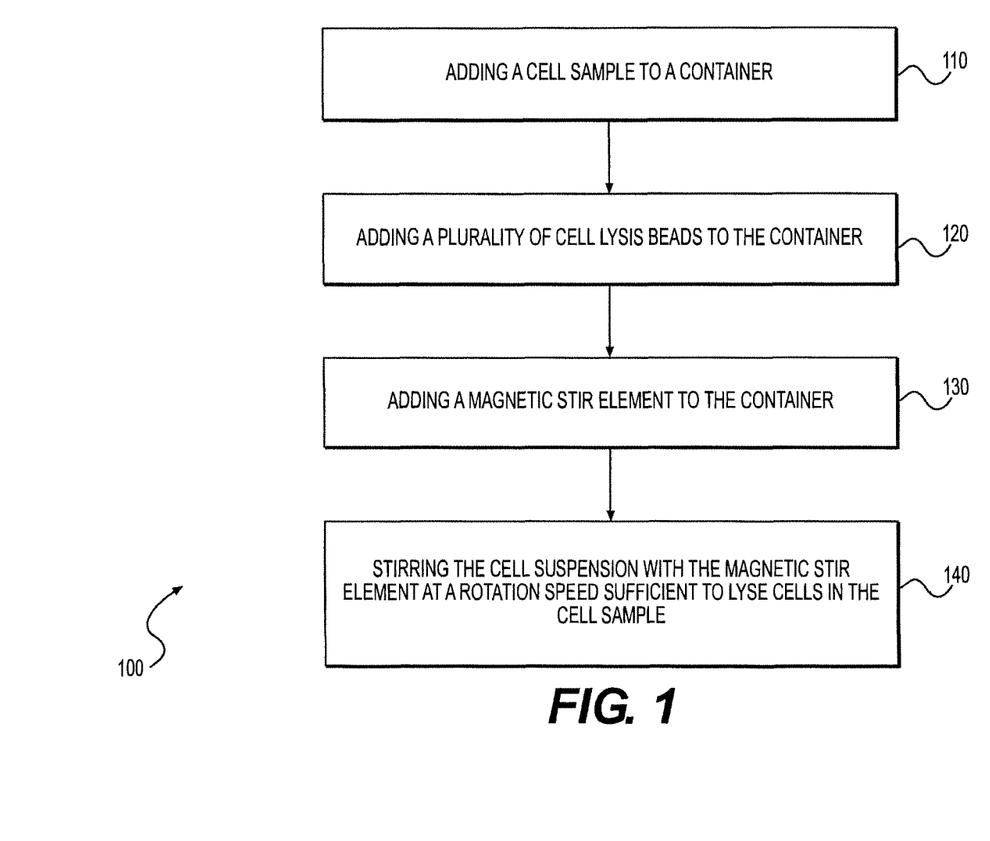
FIG. 1 is a flow chart showing an embodiment of a method for lysing cells.
Figure 2:
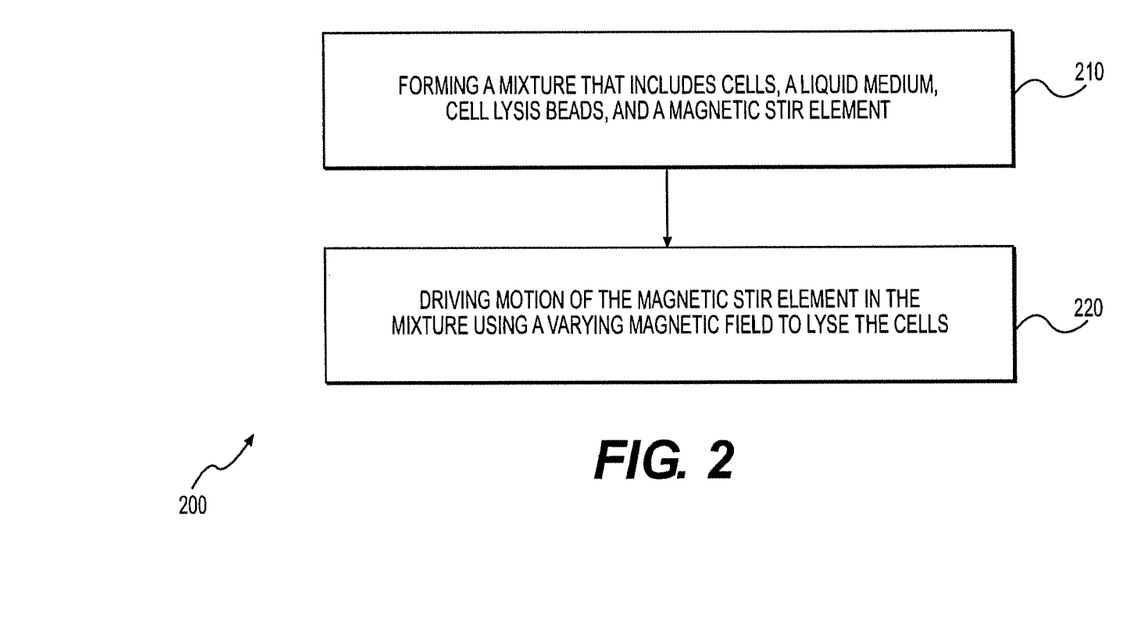
FIG. 2 is a flow chart showing another embodiment of a method for lysing cells.
Figure 3:
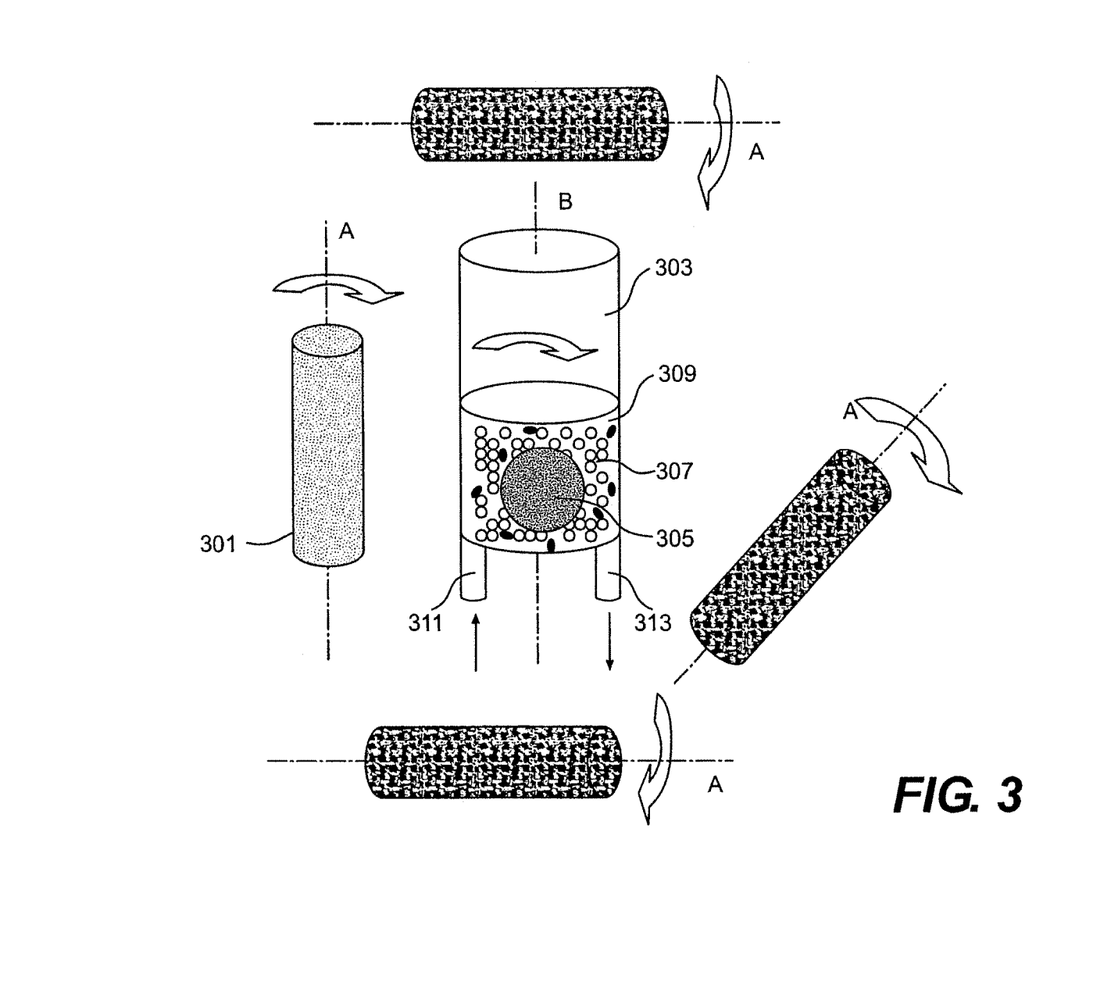
FIG. 3 is a graph showing relative positions of a magnet and a lysis chamber.

FIG. 3 shows the relative positions of a cylinder shaped magnet 301 and a lysis chamber 303. The magnet 301 rotates about an axis A and causes a magnet stir element 305 in the chamber 303 to rotate in the same direction along an axis B. The rotating magnet stir element 305 collides with beads 307 and lyse cells 309 in the process. The magnet 301 may be positioned alongside, above, below or diagonally from the chamber 303. In this embodiment, the chamber 303 has an inlet 311 and an outlet 313 to facilitate loading and unloading of the chamber.

In certain embodiments, the speed of rotation of the stirrer element is increased to increase lysis efficiency and reduces the time required to achieve lysis. In certain other embodiments, the speed of rotation is regulated so that only certain types of cells are lysed. For example, in a cell suspension containing multiple types of cells, the stir element may rotate at a first speed to lyse a first set of cells and then rotate at a second speed to lyse a second set of cells. In other embodiments, the container is coupled to a temperature regulation module that controls the temperature of the cell suspension before, during and/or after the lysing process. In certain embodiments, the temperature of the cell suspension is maintained at 8-2° C.

In certain embodiments, lysing of particular cell types can be facilitated by adding additives to the cell suspension prior to and/or during the stirring step. Examples of additives include enzymes, detergents, surfactants and other chemicals such as bases and acids. It has been found that alkaline conditions (e.g., 10 mM NaOH) may enhance the lysis efficiency during stirring for certain types of cells. The cell suspension may also or alternatively be heated during stirring to enhance the lysis efficiency. Additives, however, can be detrimental to downstream processing steps including nucleic acid amplification and detection. Eliminating the need for additives to achieve efficient lysis is desirable as specimen processing can be greatly simplified.

The stirrer/beads combination provides many advantages over conventional lysing methods. The stirrer/beads method is much faster than chemical and enzymatic approaches, and provides improved cell or virus lysis over many other types of physical lysis methods. The stirrer/beads method is also amenable to automation using robotics and/or microfluidics. The magnetic source is reusable and doesn't require precise alignment with the vessel, can drive a plurality of chambers. The magnetic stirrer element is low-cost to enable it to be single-use disposable.

Also disclosed is a device for lysing cells. The device includes a chamber having a magnetic stir element and a plurality of cell lysis beads disposed therein. A user may simply add a cell suspension into the chamber, place the chamber on a magnetic stirrer, and stir the cell suspension with the magnetic stir element at a speed sufficient to lyse the cells.

Also disclosed is a system for lysing cells. The system includes a chamber having a magnetic stir element and a plurality of cell lysis beads disposed therein, and a magnetic stirrer that produces a rotating magnetic field, wherein the magnetic stir element rotates inside the chamber when placed within an operational range of the rotating magnetic field.

In certain embodiments, the system further contains a rack configured to hold the chamber. The rack may be configured to hold multiple chambers and can be placed on a support surface of a magnetic stirrer for simultaneous processing of multiple samples. The rack may also be used as holder of the chamber for storage purpose. For example, multiple chambers may be placed on the rack and stored in a refrigerator or freezer for further analysis. The chamber may be interfaced with an external instrument (e.g. liquid handling robot, microfluidic device, analytical instrument).

Also disclosed is a method for purifying nuclei acid from a cell. The method comprises applying a magnetic field to a vessel containing a cell, a stir element, and a plurality of beads, wherein the magnetic field causes the stir element to collide with the plurality of beads and produce a cell lysate; and isolating nuclei acid from the cell lysate.

Also disclosed is a method for amplifying a polynucleotide from a cell. The method comprises applying a magnetic field to a vessel containing a cell, a stir element, and a plurality of beads, wherein the magnetic field causes the stir element to collide with the plurality of beads and produce a cell lysate, and amplifying a polynucleotide from the cell lysate.

Also disclosed is a method for detecting a polynucleotide from a cell. The method comprises applying a magnetic field to a vessel containing a cell, a stir element, and a plurality of beads, wherein the magnetic field causes the stir element to collide with the plurality of beads and produce a cell lysate, and detecting a polynucleotide from the cell lysate. In certain embodiments, the detecting step comprises isolating nuclei acids from the cell lysate, amplifying the polynucleotide from isolated nuclei acids, and detecting the amplified polynucleotide.

EXAMPLES

Example 1

Lysis of *E. coli* Cells

*E. coli* cells were suspended in Tris-EDTA buffer at a concentration of $10^4$ cells/ml One milliliter of the cell suspension was added to a chamber (2 ml plastic vial, Wheaton) containing 800 mg glass beads (106 µm or finer, Sigma G8893) and a magnetic stir disc (VP-7195 Super Tumble Stir Disc, V&P Scientific).

The plastic vial was then placed on a magnetic stirrer (VP 710C1 Rotary Magnetic Tumble Stirrer, 5000 RPM, V&P Scientific) and stirred at 5000 rpm for 30 seconds, 1 minute or 2 minutes. Positive control samples were processed using a bead beater (Mini Bead Beater-1, Biospec) according to the manufacturer's instructions for 2 minutes at 4800 rpm. Unprocessed cell suspensions were used as controls. The lysed cells and controls were then subjected to real-time PCR amplification of a specific gene using a Roche Light-Cycler 480. The amplification conditions were: 95° C. for 250 sec; then 45 cycles at 95° C. for 10 sec, 60° C. for 20 sec, and 72° C. for 10 sec; and 40° C. for 10 sec at the final cycle.

Figure 4:
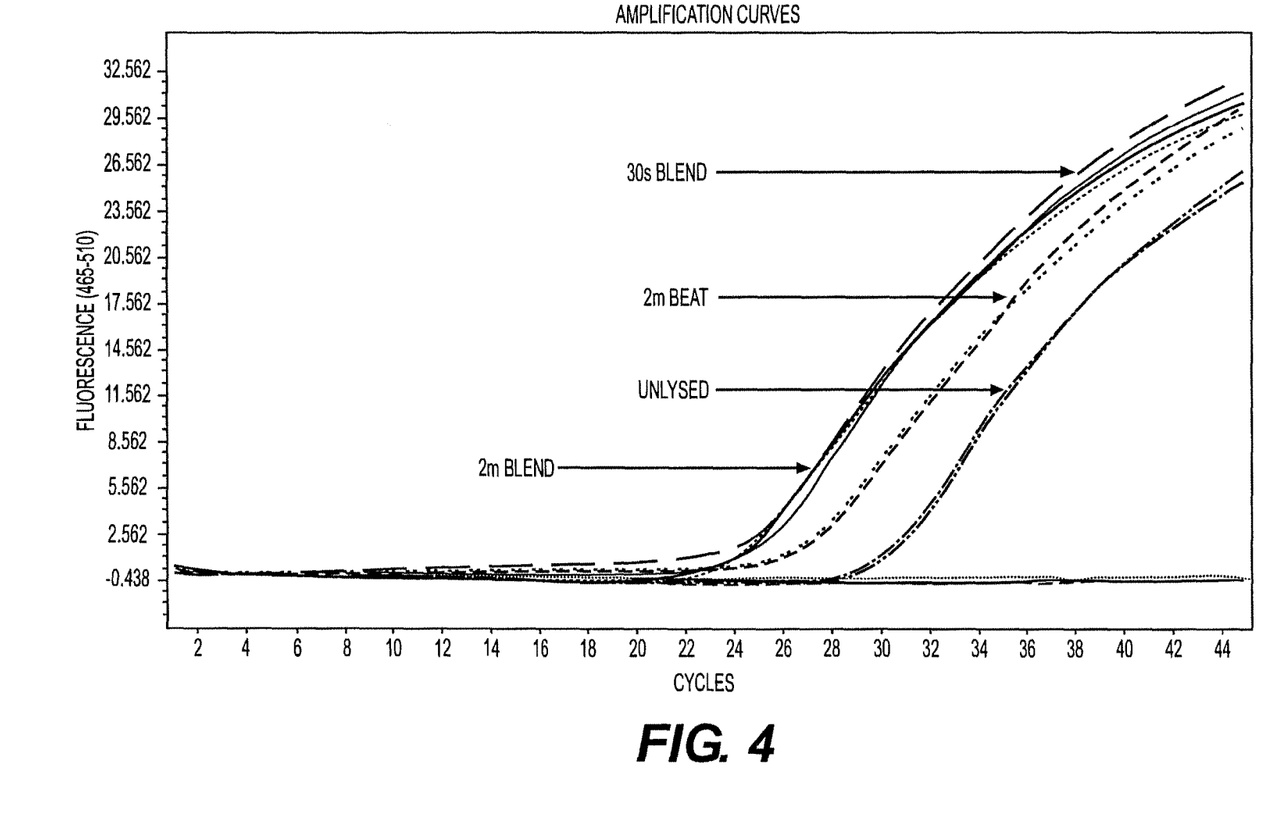
FIG. 4 is a graph showing real-time PCR amplification of a specific genomic region from unlysed E. coli cells (unlysed), E. coli cells lysed by bead beater for 2 minutes (2m beat), and E. coli cells lysed by beads/stirrer for 30 seconds (30s blend) or 2 minutes (2m blend).
Figure 5:
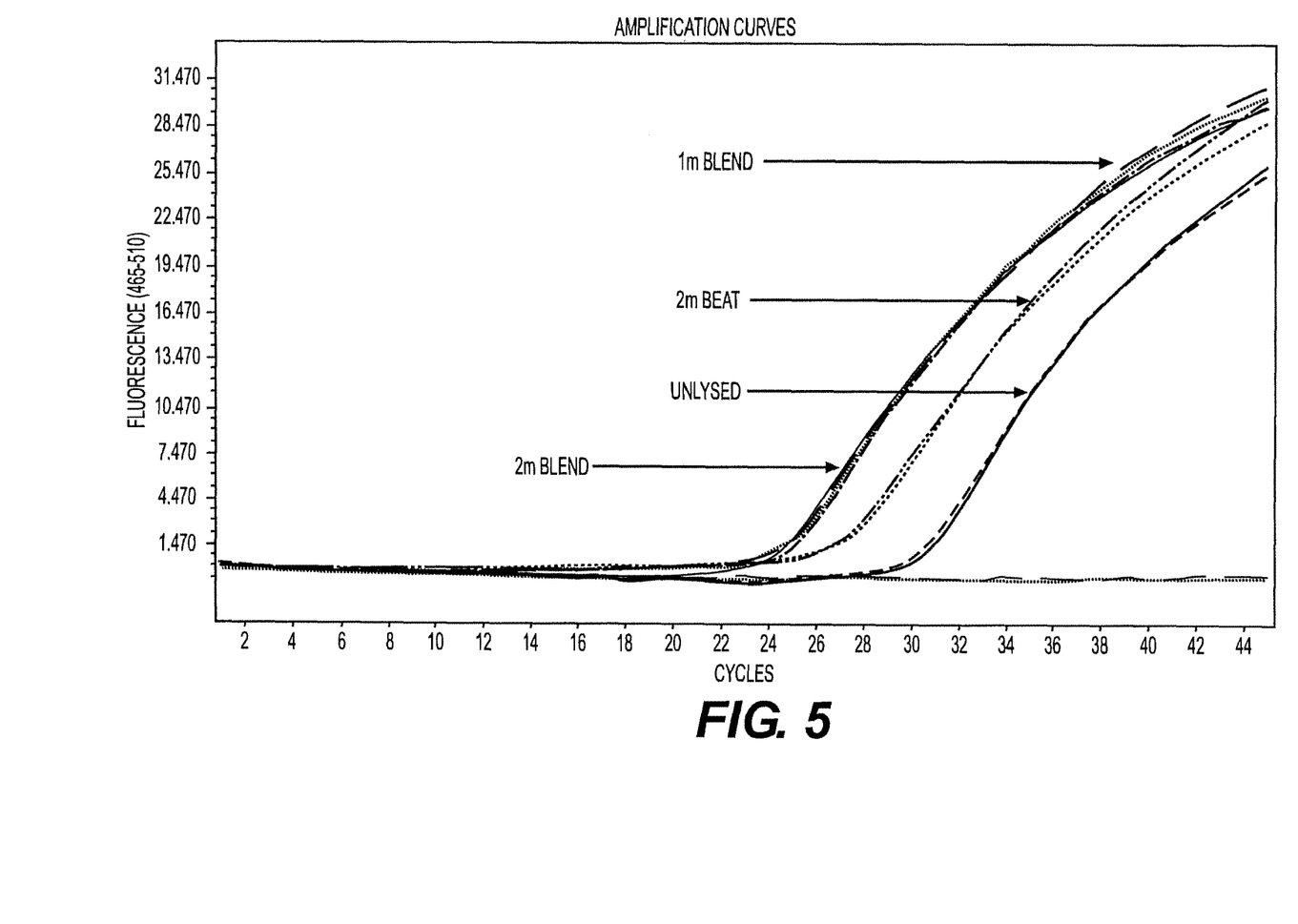
FIG. 5 is a graph showing real-time PCR amplification of a specific genomic region from unlysed E. coli cells (unlysed), E. coli cells lysed by a bead beater for 2 minutes (2m beat), and E. coli cells lysed by beads/stirrer for 1 minute (1m blend) or 2 minutes (2m blend).
Figure 6:
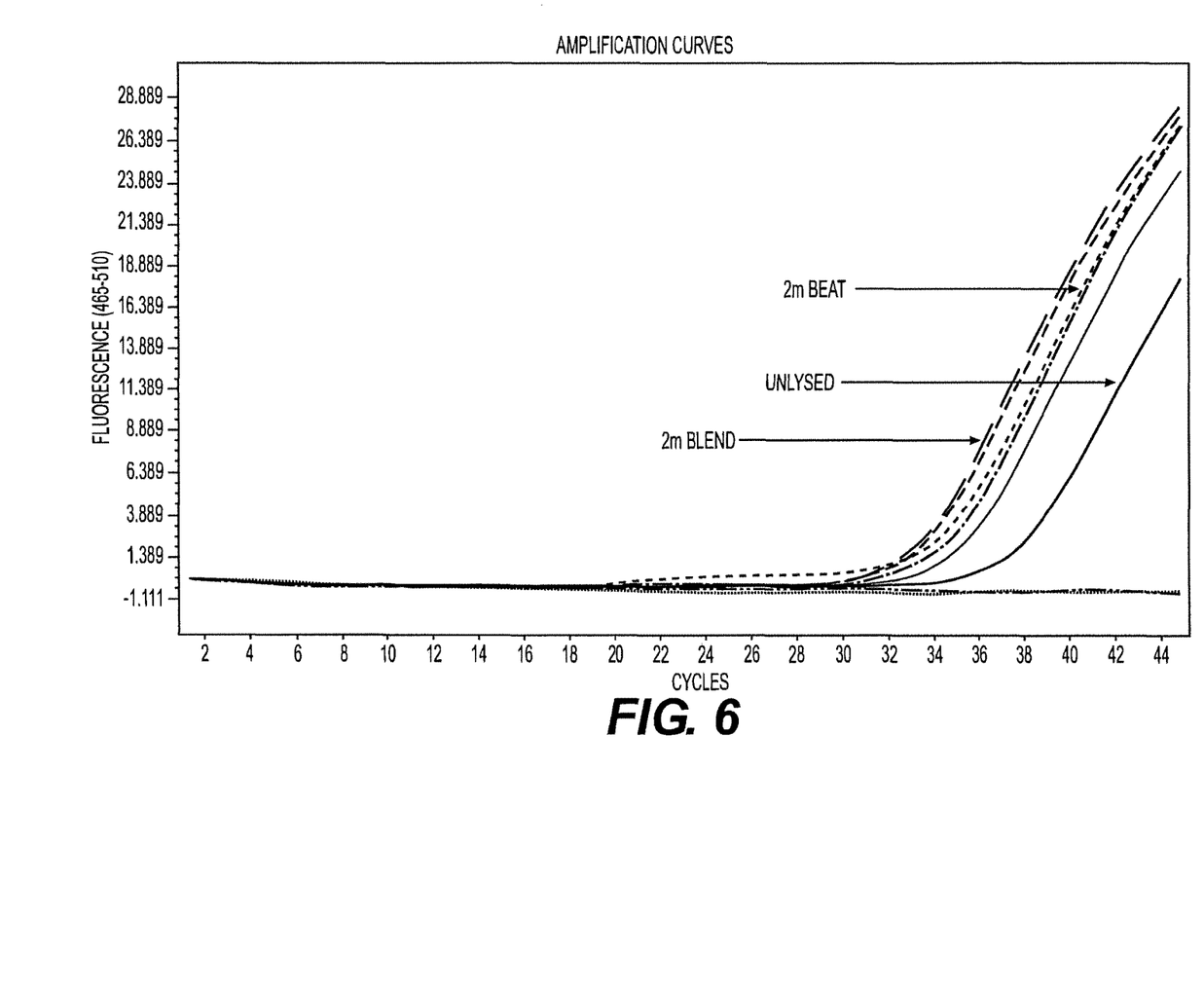
FIG. 6 is a graph showing real-time PCR amplification of a specific genomic region from unlysed *Bacillus thuringiensis* spores (unlysed), *Bacillus thuringiensis* spores lysed by a bead beater for 2 minutes (2m beat), and *Bacillus thuringiensis* spores lysed by beads/stirrer for 2 minutes (2m blend).
Figure 7:
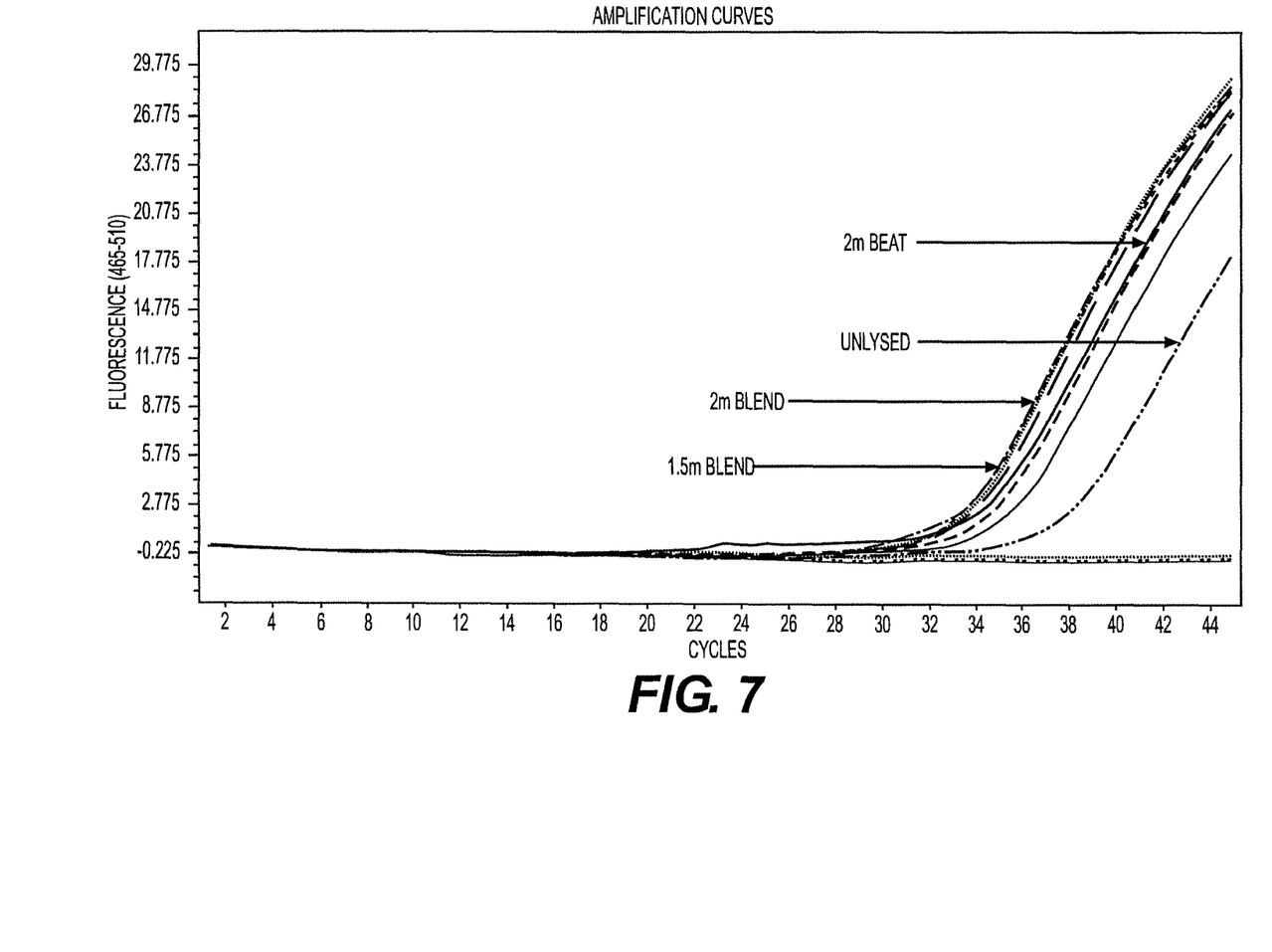
Figure 8:
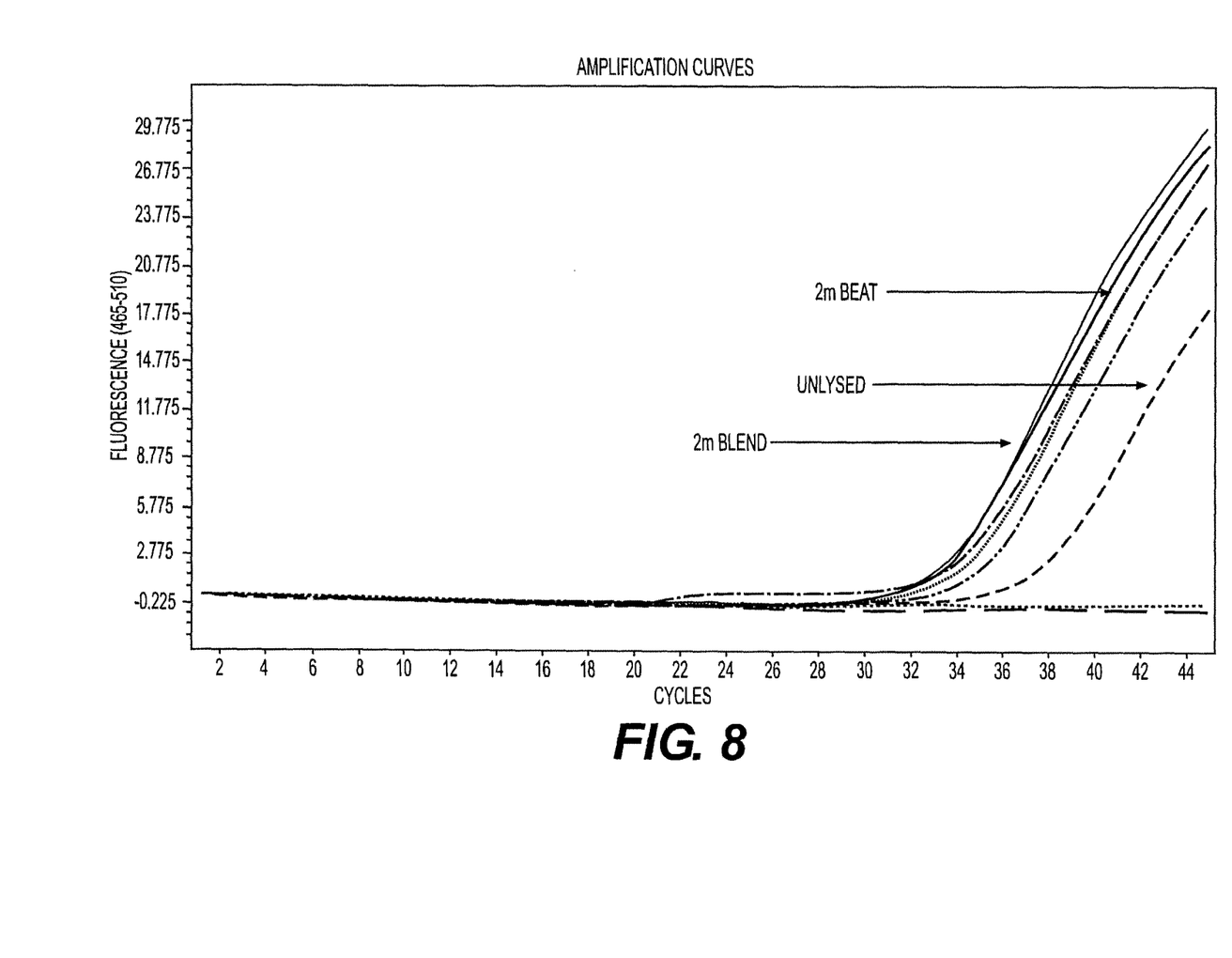
Figure 9:
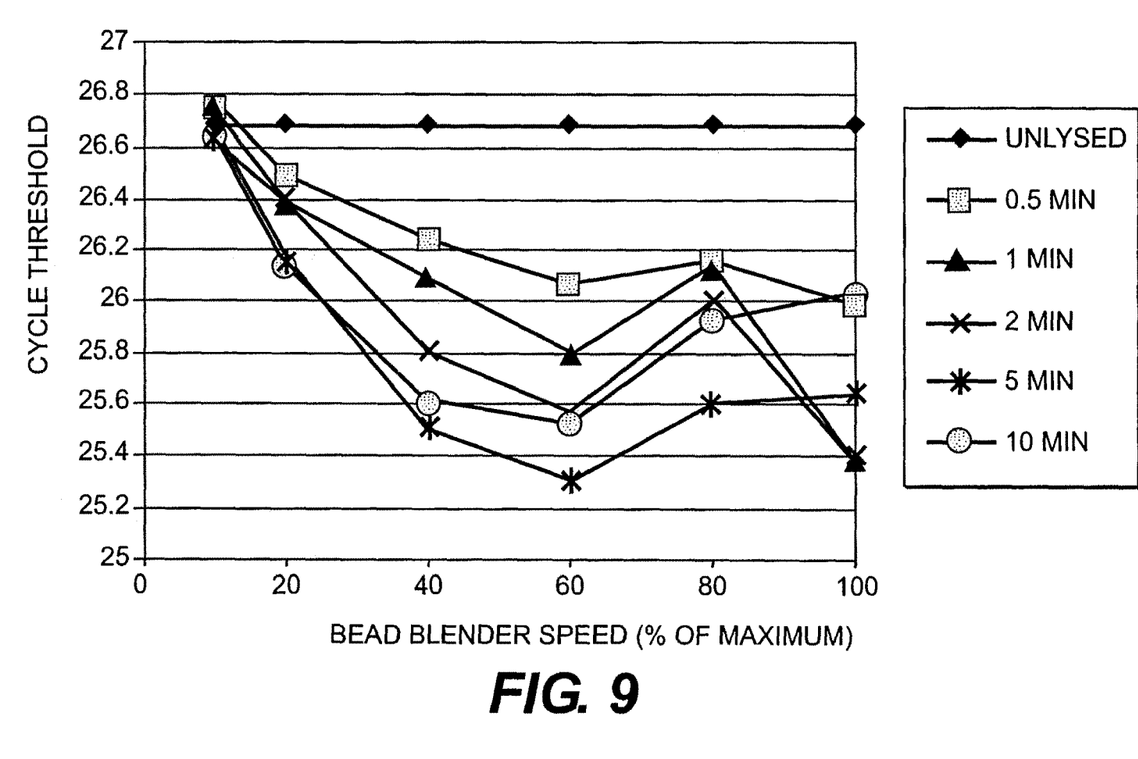
Figure 10:
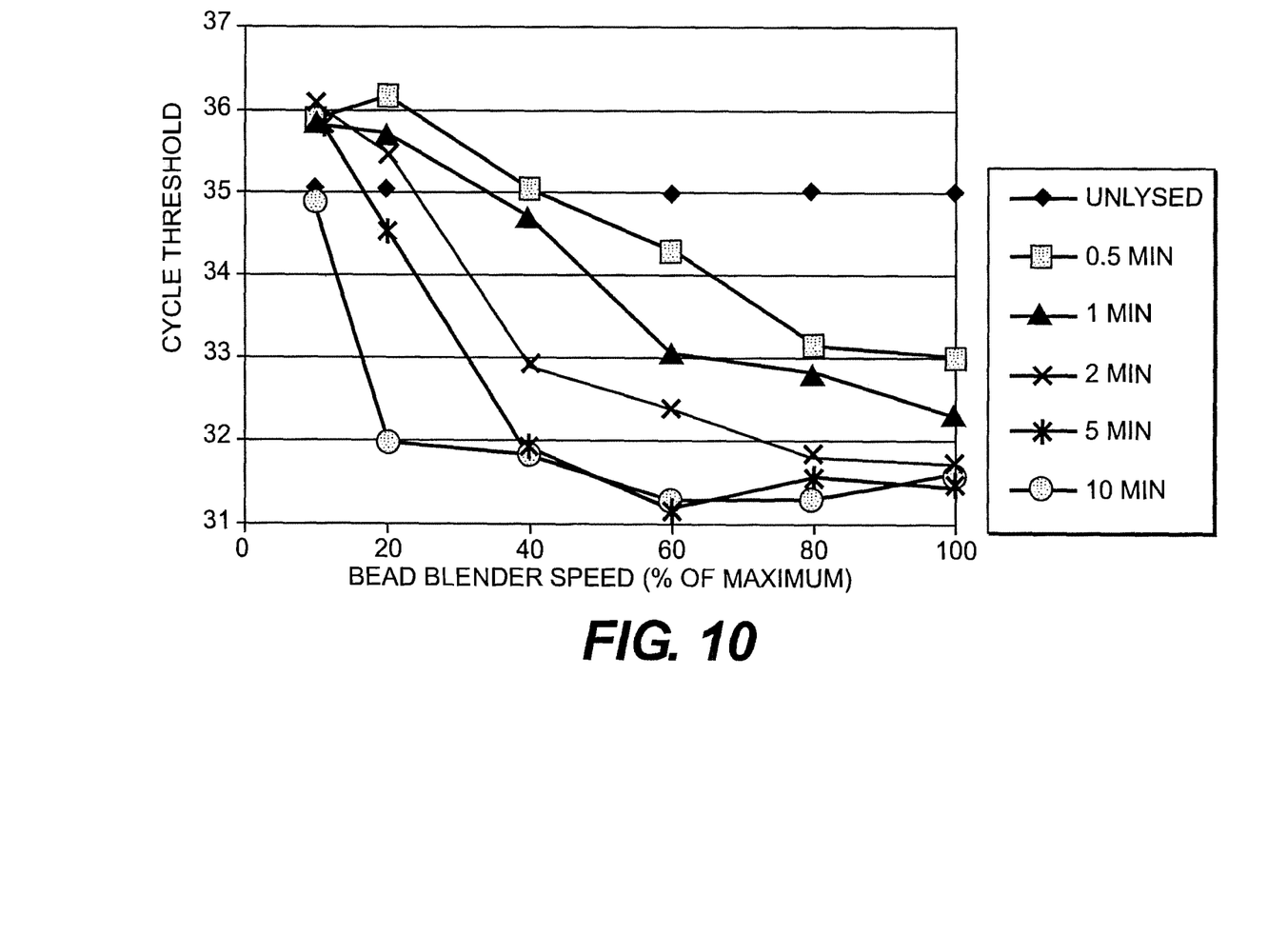

As shown in FIGS. 4 and 5, the beads/stirrer method (30s blend, 1 m blend and 2m blend) provides better cell lysis than the bead beater method (2m beat).

Example 2

Lysis of *Bacillus thuringiensis* Spores

*Bacillus thuringiensis* spores were suspended in water at a concentration of $10^4$ cells/ml. 500 µl of the cell suspension was added to a 2 ml plastic vial (Wheaton) containing 800 mg of glass beads (106 μm or finer, Sigma) and a magnetic stir disc (VP-7195 Super Tumble Stir Disc, V&P Scientific).

The plastic vial was then placed on a magnetic stirrer (VP 710C1 Rotary Magnetic Tumble Stirrer, 5000 RPM, V&P Scientific) and stirred at 5000 rpm for 1.5 minute or 2 minutes. Positive control samples were processed using a bead beater (Mini Bead Beater-1, Biospec) according to the manufacturer's instructions for 2 minutes. Unprocessed cell suspensions were used as controls. The lysed cells and controls were then subjected to real-time PCR amplification of a specific *B. thuringiensis* gene using a Roche LightCycler 480 under conditions described in Example 1.

As shown in FIGS. 3-6, the beads/stirrer method (1.5 m blend and 2m blend) provides better cell lysis than the bead beater method (2m beat).

Example 3

Effect of Lysis Time and Bead Blender Speed on the Real-time PCR Response for *Staphylococcus aureus* Cells

*Staphylococcus aureus* cells were suspended and lysed at various blender speeds for various time periods using the same equipment and procedures described in Example 2.

FIG. 9 is a graph showing the effect of lysis time and bead blender speed on the real-time PCR response for *Staphylococcus aureus* cells. Efficient lysis of *S. aureus* cells was achieved in 2 minutes when the bead blender was operated at high-speed. Lower speeds required longer lysis times. Unlysed spores have low-levels of extracellular DNA that are detectable without lysis (0 min) A small amount of free DNA binds to the glass beads. Bead blender speed of 100 corresponds to 5000 rpm.

Example 4

Effect of Lysis Time and Bead Blender Speed on the Real-time PCR Response for *Bacillus thuringiensis* Spores

*Bacillus thuringiensis* spores were suspended and lysed at various blender speeds for various time periods using the same equipment and procedures described in Example 2.

FIG. 10. is a graph showing the effect of lysis time and bead blender speed on the real-time PCR response for *Bacillus thuringiensis* spores. Efficient lysis of *Bacillus*

*thuringiensis* spores was achieved in 2 minutes when the bead blender was operated at high-speed. Lower speeds required longer lysis times. Unlysed spores have low-levels of extracellular DNA that are detectable without lysis (0 min). A small amount of free DNA binds to the glass beads. Bead blender speed of 100 corresponds to 5000 rpm.

The invention claimed is:

1. A device for lysing cells, comprising:

a chamber, wherein inside of the chamber contains a magnetic stir element and a plurality of beads, wherein the chamber is dimensioned to allow rotation of the magnetic stir element inside the chamber and wherein the chamber is placed on a surface; and a magnet in the proximity of the chamber and not below the chamber, wherein the magnet is located above the bottom of the chamber and produces a varying magnetic field by rotating the magnet along an axis that is located above the bottom of the chamber and is parallel to the surface the chamber is placed on or the magnet is located on a side of the chamber, and produces a varying magnetic field by rotating the magnet along an axis that is located on the side of the chamber, wherein the axis passes through the center of the magnet, and wherein the chamber is in operational range of the varying magnetic field such that motions of the magnet stir element and the plurality of beads inside of the chamber are driven by the varying magnetic field.

2. The device of claim 1, further comprising a temperature control module that controls the temperature of the chamber.

3. The device of claim 1, wherein the plurality of heads comprise a material selected from the group consisting of plastics, glass, ceramics, metals and mixtures thereof.

4. The device of claim 1, wherein the plurality of beads comprise silica beads.

5. The device of claim 1, wherein the plurality of beads have diameters within the range of 10-1000 μm.

6. The device of claim 1, wherein the magnetic stirrer element comprises a metal or an alloy.

7. The device of claim 1, wherein the magnetic stirrer element comprises an alloy core coated with a polymer.

8. The device of claim 7, wherein the alloy core comprises neodymium iron boron or samarium cobalt and/or wherein the polymer is a biocompatible polymer, optionally polytetrafluoroethylene (PTFE) or parylene.

* * * * *